(12) United States Patent
Almiñana Domenech et al.

(10) Patent No.: US 7,943,156 B2
(45) Date of Patent: May 17, 2011

(54) USE OF PEPTIDES OF GENERAL FORMULA I X-SEQ ID NO.1-Y IN THE PREPARATION OF COSMETIC COMPOSITIONS WHICH ARE INTENDED TO IMPROVE THE FIRMNESS OF THE SKIN BY INCREASING CELL ADHESION

(75) Inventors: Nuria Almiñana Domenech, Barcelona (ES); José María Garcia Anton, Barcelona (ES); Juan Cebrián Puche, Barcelona (ES); Arturo Puig Montiel, Barcelona (ES)

(73) Assignee: Lipotec, S.A., Barcelona (ES)

( * ) Notice: Subject to any disclaimer, the term of this patent is extended or adjusted under 35 U.S.C. 154(b) by 168 days.

(21) Appl. No.: 11/587,878

(22) PCT Filed: Apr. 5, 2005

(86) PCT No.: PCT/ES2005/000175
§ 371 (c)(1),
(2), (4) Date: Oct. 17, 2007

(87) PCT Pub. No.: WO2005/105029
PCT Pub. Date: Nov. 10, 2005

(65) Prior Publication Data
US 2008/0085852 A1    Apr. 10, 2008

(30) Foreign Application Priority Data
Apr. 28, 2004 (ES) .................. 200401018

(51) Int. Cl.
*A61K 8/64* (2006.01)
*A61K 38/08* (2006.01)

(52) U.S. Cl. ...... 424/401; 514/18.6; 514/18.8; 514/21.8
(58) Field of Classification Search .................... None
See application file for complete search history.

(56) References Cited

U.S. PATENT DOCUMENTS

| | | | |
|---|---|---|---|
| 5,744,515 A | 4/1998 | Clapper | 523/113 |
| 6,428,579 B1 | 8/2002 | Valentini | 623/23.76 |

(Continued)

FOREIGN PATENT DOCUMENTS

EP    1325739 A1    7/2003

(Continued)

OTHER PUBLICATIONS

Grant et al. Revascularization of Ischemic Tissues with SIKVAV and Neuropeptide Y (NPY). 2000. Angiogenesis: From the Molecular to Integrative Pharmacology, pp. 139-154.*

(Continued)

*Primary Examiner* — Jeffrey E Russel
(74) *Attorney, Agent, or Firm* — Ohlandt, Greeley, Ruggiero & Perle, LLP

(57) ABSTRACT

The invention relates to cosmetic compositions which are intended to improve the firmness of the skin by increasing adhesion of cutaneous cells in relation to one another and the basal lamina. The aforementioned compositions comprise a cosmetically-effective quantity of peptides having general formula X-isoleucyl-lysyl-valyl-alanyl-valine-Y, known as X-SEQ ID No. 1-Y (FIG. 1). The invention also relates to the use of X-SEQ ID No. 1-Y peptides in the preparation of cosmetic compositions which are intended to improve the firmness of the skin.

14 Claims, 5 Drawing Sheets

U.S. PATENT DOCUMENTS 6,673,108 B2    1/2004    Zilla et al. .................. 623/1.4

FOREIGN PATENT DOCUMENTS

| JP | 3197411 | | 8/1991 |
| JP | 2002-45419 A | * | 2/2002 |
| WO | WO 98/43686 | | 10/1998 |
| WO | WO 03/007905 A2 | | 1/2003 |

OTHER PUBLICATIONS

Machine Translation of JP 2002-45419 (Feb. 12, 2002).*
Translation of Japanese Patent Application 2002-45419, published Feb. 12, 2002, titled "Wound Coating Material".*

Almiñana-Domenech, N. et al. "Synthesis, interaction with phospholipids and biological activity of the laminin active sequence: SIKVAV." Journal of Peptide Science, 2002, vol. 8, p. S146 © 2002 European Peptide Society and John Wiley & Sons, Inc.

LeVarlet, B. et al., "Age-Related Functional and Structural Changes in Human Dermo-Epidermal Junction Components." LVMH Recherche, Parfums Christian Dior, Symposium Proceedings, Journal for Investigative Dermatology 1998, pp. 172-179.

Grant, D.S., et al.,"Interaction of Endothelial Cells With a Laminin A Chain Peptide (SIKVAV) In Vitro and Induction of Angiogenic Behavior in Vivo." Journal of Cellular Physiology 153:614-625 © 1992 Wiley-Liss Inc.

* cited by examiner

USE OF PEPTIDES OF GENERAL FORMULA I X-SEQ ID NO.1-Y IN THE PREPARATION OF COSMETIC COMPOSITIONS WHICH ARE INTENDED TO IMPROVE THE FIRMNESS OF THE SKIN BY INCREASING CELL ADHESION

FIELD OF THE INVENTION

The present invention relates to cosmetic compositions which are intended to improve the firmness of the skin, by increasing adhesion of cutaneous cells in relation to one another and the basal lamina. The aforementioned compositions comprise a cosmetically-effective quantity of peptides having general formula I X-SEQ ID NO.1-Y, where X can be H, an amino acid or a linear or branched chain acyl group (see FIG. 1) and Y can be amino, hydroxyl or thiol, all of them substituted or non-substituted with fatty acids:

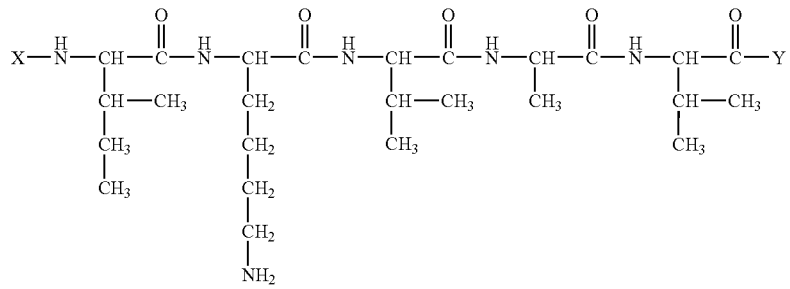

STATE OF THE ART

The skin is the largest organ of the human body. Two layers can be distinguished: the epidermis and the dermis. These two layers are joined through the basement membrane, a matrix formed by different macromolecules (collagen, laminin, proteoglycans, etc.).

The basal lamina is rich in type IV collagen, proteoglycans and in the glycoproteins entactin and laminin.

These molecules provide a structural network as well as bioadhesive properties for cell binding. The laminin sequence contains several binding domains: for type IV collagen, for perlecan (heparan sulphate proteoglycan), for entactin and for the receptors in the cell surface.

This basement membrane is a specialized extracellular matrix formed by three layers:

Lamina lucida: this layer is directly in contact with basal keratinocytes, and its main component is laminin.

Lamina densa: it is located under the lamina lucida and extends parallel to the latter with a similar thickness. It is an amorphous material in which collagen IV predominates, responsible for the great traction strength and for the flexibility of the basement membrane.

Reticular lamina: it is under the previous layers, but its location is more inaccurate, and is originated by the fibroblasts of the dermis. It is formed by anchoring fibrils and elastic microfibrils which are introduced in the lamina densa, with which they hold the basement membrane and provide cohesion to the cutaneous tissue. The anchoring fibrils are structures formed by collagen VII.

Laminin is found in the first of the mentioned laminas, the lamina lucida, and is the main component thereof.

Laminin is a glycoprotein of about 850 kDa and after collagen it is the most abundant protein in the extracellular matrix (ECM). Laminin is found exclusively in the basement membranes and is formed by three long polypeptide chains (alpha, beta and gamma) distributed in a cross shape and joined by disulphide bridges.

The three chains exist in different laminin subtypes and their combinations result in a dozen different laminin isoforms, among which laminin-1 is the most studied.

Integrins are the most important of the receptors involved in the recognition of laminin and they are the first ECM receptors that were discovered. They are a group of transmembrane cell surface receptors in charge of cell-cell and cell-ECM interactions.

Cells recognize binding domains in laminin through receptor integrins, giving as a result the binding of the latter to the basement membrane rich in laminins. The receptor integrins also mediate in the binding between cells through specific ligands.

Cutaneous aging is one of the dermal processes experienced by the skin and is a common biological process in all living organisms.

A loss of the functional capacity of the skin and an increase of vulnerability, characterized by a dry, wrinkled, yellowish skin with spots, grayish hair, as well as tissue slackness and relaxation, etc., is generally observed when the cutaneous aging process takes place.

It has been observed that the adhesion of epidermis cells to the basement membrane starts decreasing after the age of 30. This loss of contact between the dermis and the epidermis produces structural and functional changes in the skin which form part of the aging process [*J. Investig. Dermatol. Symp. Proc.* 1998; 3 (2):172-9].

It is therefore possible to prevent and improve the relaxation and loss of firmness of the skin by increasing the adhesion between the cells and the basement membrane, thus delaying skin aging.

In this sense, inventions relating to the use of peptides of general formula X-SEQ ID NO.1-Y in cosmetic compositions so as to increase the firmness of the skin and delay the aging thereof have not yet been described in the state of the art.

U.S. Pat. No. 5,744,515 [Method and implantable article for promoting endothelialization] relates to implants made of polymeric, ceramic and metallic materials with a surface coated with adhesive molecules, such as fibronectin, laminin, collagen, and domains thereof. SEQ ID No. 2 is one of the domains described among those domains and is specifically described as a domain of the protein fibronectin. The adhesive molecules are included to promote endothelialization of the implant and its adhesion to cells and the implant is made of porous biomaterial to allow the growth of capillaries through the material.

On the other hand, U.S. Pat. No. 6,428,579 [Implantable prosthetic devices coated with bioactive molecules], relates to a implant coated with gold on which bioactive peptides with different types of properties, such as cell modulating, chemotactic, anticoagulant, antithrombotic, anti-tumor, anti-infectious, growth enhancing, anti-inflammatory properties, etc., are adhered. SEQ ID No. 2, among others, is mentioned as an example of a cell modulating peptide within the group of integrin binding peptides. A preferred use of these implants is to accelerate bone growth after trauma surgery, and integrin substrate peptides, for example SEQ ID No. 2, are used to improve peptide adhesion to bone tissue.

U.S. Pat. No. 6,673,108 [Transmural concentric multilayer ingrowth matrix within well-defined porosity] relates to a matrix with several synthetic or proteinaceous layers. Each layer has a specific function. A fibrin layer derivatized with peptides or growth factors, and specifically a fibrin layer with peptides derived from laminin such as SEQ ID No. 2, is named as an example of a proteinaceous layers.

None of these patents mentions the use of peptides of general formula X-SEQ ID No. 1-Y in cosmetic compositions.

Therefore, the basis of the present invention is to provide a cosmetic composition capable of increasing the firmness of the skin, thus delaying the aging thereof.

DESCRIPTION OF THE INVENTION

Peptides of general formula X-SEQ ID No. 1-Y form a chemotactic region in laminin, i.e. a cell attraction region. This is the reason why these peptides promote cell adhesion, growth and migration, thus regenerating the basal lamina. Angiogenesis stimulation (formation of new blood vessels) properties, which promote the proliferation and differentiation of endothelial cells, are also known in these peptides [*Journal of Cellular Physiol.* 1992 December; 153(3): 614-25].

The interactions between peptides of form X-SEQ ID No. 1-Y and receptor integrins are known and their use is described in patent number EP 1 325 739 ["Liposomes encapsulating anticancer drugs and the use thereof in the treatment of malignant tumors"] where the over-expression of laminin receptors in the membranes of tumor cells is used to steer towards the latter liposomes coated with X-SEQ ID NO:1-Y peptides containing anti-tumor agents.

It has now been determined that X-SEQ ID No. 1-Y peptides have different cosmetic application functions at the level of cutaneous cells, which are the following:

Stimulation of keratinocyte adhesion (see FIG. 8) in the presence of X-SEQ ID No. 1-Y peptides, such as SEQ ID No. 1, SEQ ID No. 2 or Pal-SEQ ID No. 1, where X is the H, seryl or palmitoyl radical, respectively.

Figure 2:
FIG. 2 shows the expression of α6 integrin in fibroblasts for the control sample, in which SEQ ID NO. 2 was not added.
Figure 3:
FIG. 3 shows the stimulation of the expression of α6 integrin in fibroblasts in presence of SEQ ID NO.2.

Stimulation of the expression of α6 integrin in fibroblasts, as observed in FIG. 3, in which the occurrence of fluorescence is observed in the presence of X-SEQ ID No 1-Y, when α6 integrin is expressed in contrast to FIG. 2 which shows what occurs in the control sample in which X-SEQ ID No. 1-Y is not added.

Figure 4:
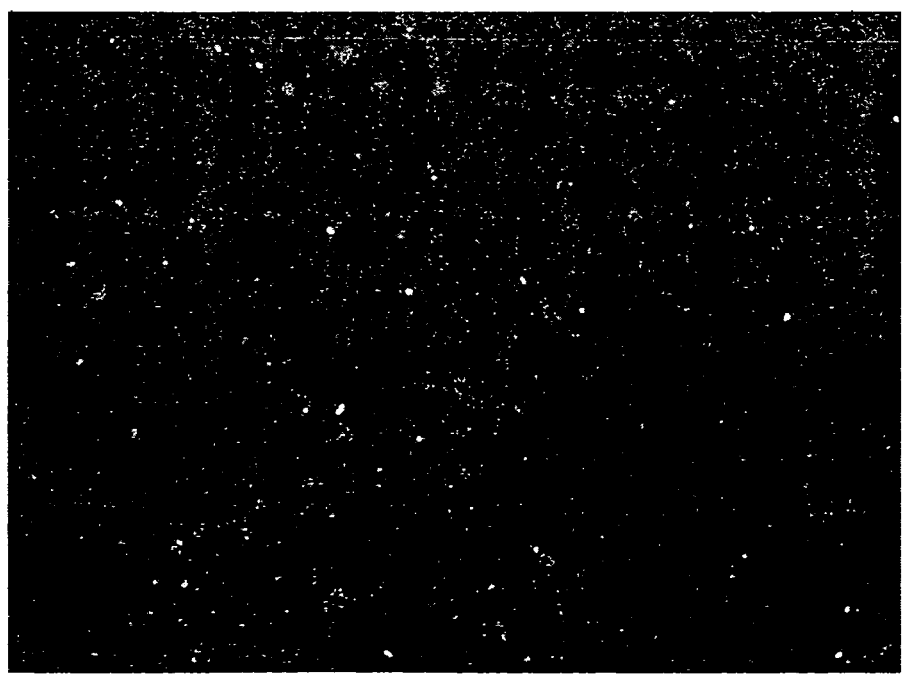
FIG. 4 shows the expression of laminin V in fibroblasts for the control sample, in which SEQ ID NO.2 was not added.
Figure 5:
FIG. 5 shows the stimulation of the expression of laminin V in fibroblasts in presence of SEQ ID NO.2.

Stimulation of the expression of laminin V in fibroblasts is observed by the occurrence of fluorescence, as seen in FIG. 5, in the presence of X-SEQ ID No. 1-Y peptides. A control sample without X-SEQ ID No. 1-Y peptides was used to observe the effect of the expression of laminin V (see FIG. 4).

A cosmetic composition including peptides of general formula X-SEQ ID No. 1-Y capable of increasing the firmness of the skin, thus delaying the aging thereof, has been designed in the present invention.

Assays have been carried out to quantify the increase of cell adhesion of keratinocytes and fibroblasts, as well as the generation of integrins, laminins, etc.

In summary, X-SEQ ID No. 1-Y peptides are capable of favoring keratinocyte adhesion by themselves and stimulating the synthesis by fibroblasts of laminin V and α6 integrin (bioadhesion peptides), both of which are involved with the hemidesmosomes which are essential structures for the dermal-epidermal junction.

Likewise, the aforementioned microcirculation stimulation together with the good condition of the basement membrane will aid in the suitable transport of oxygen and metabolites, as well as in the elimination of excretion products, thus improving the functional capacity of epidermal cells and at the same time their resistance and firmness.

Therefore, the use of X-SEQ ID No. 1-Y peptides incorporated in a cosmetic composition of topical application has a direct effect on the prevention of skin aging, delaying the loss of contact between the dermis and the epidermis and preventing the structural and functional changes forming part of the aging process.

Figure 1:
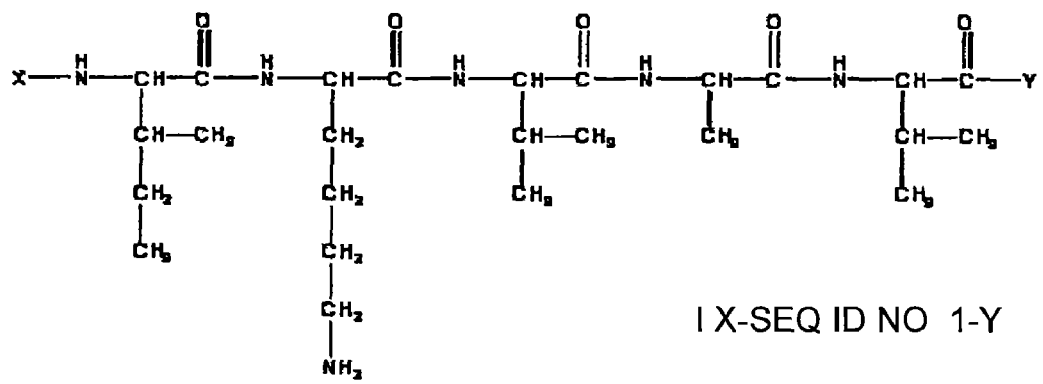
FIG. 1 shows the peptides of general formula I, X-SEQ ID NO. 1-Y.

Therefore, according to a first aspect of the invention, the latter relates to the use of peptides of general formula X-SEQ ID No. 1-Y (see FIG. 1), where X is selected from the group formed by H, an amino acid or a linear or branched chain acyl group, and Y can be amino, hydroxyl or thiol, all of them substituted or non-substituted with fatty acids, for the stimulation of cutaneous cell bioadhesion by means of increasing the expression of bioadhesion peptides.

Preferably, in the peptides of general formula I, X is hydrogen, serine, palmitoyl or decanoyl and Y can be amino, hydroxyl or thiol, all of them substituted or non-substituted with fatty acids.

Preferably, in the peptides of general formula I, X is serine and Y is hydroxyl, i.e. the SEQ ID No. 2 peptide.

Preferably, in the peptides of general formula I, X is hydrogen and Y is hydroxyl, i.e. the SEQ ID No. 1 peptide.

Preferably, the cutaneous cells in which bioadhesion is stimulated are keratinocytes and the bioadhesion peptides are α6 integrin and laminin V.

According to a second aspect of the invention, the latter relates to a cosmetic composition comprising, in a cosmetically acceptable medium, a cosmetically-effective quantity of peptides having general formula X-SEQ ID No. 1-Y for the stimulation of cutaneous cell bioadhesion by increasing the expression of bioadhesion peptides.

Said composition is preferably of dermal application.

According to a preferred embodiment, said composition increases the firmness of the skin and this effect is caused by increasing the adhesion of cutaneous cells in relation to one another and the basal lamina.

In the present invention, the X-SEQ ID No. 1-Y peptides (see FIG. 1) are preferably incorporated in a cosmetic composition in a concentration of up to 12%.

In the present invention, the X-SEQ ID No. 1-Y peptides (see FIG. 1) are preferably incorporated in a cosmetic composition in a concentration of preferably 5%.

The preferred excipients are those commonly used in cosmetics: water, alcohols, lecithins, natural or artificial polymers, surfactants and active surface agents, preservatives, etc.

The preferred cosmetic forms are those commonly used: creams, lotions, emulsions, shampoos, serums, gels, etc.

According to a preferred embodiment, the composition comprises the following ingredients in the following percentages by weight:

| INGREDIENT | % |
|---|---|
| X-SEQ ID No. 1-Y | 0.001-10 |
| Petrolatum | 0-10 |
| Triethanolamine | 0-10 |
| BHT | 0-10 |
| Phenoxyethanol, Methylparaben, Butylparaben, Ethylparaben, Propylparaben, Isobutylparaben | 0-10 |
| Stearic acid | 0-10 |
| Beeswax | 0-10 |
| Carbomer | 0-10 |
| Dimethiconol | 0-10 |
| Cyclomethicone | 0-1 |
| Glycerin | 0-10 |
| Cetylstearic alcohol | 0-10 |
| Perfume | 0-10 |
| Water | 0-99.999 |

Other active ingredients used as part of the cosmetic composition can be vitamins, natural extracts, ferments and other common ingredients for the various uses of cosmetic formulations: anti-aging, anti-cellulite, moisturizing, regenerating, revitalizing ingredients, etc.

According to another aspect, the present invention relates to the use of peptides of general formula X-SEQ ID No. 1-Y in the preparation of a cosmetic composition increasing the firmness of the skin.

Since cells use integrins to recognize laminins, and laminins bind cells through integrins, the cosmetic composition according to the present invention will enhance cell adhesion and their binding to the basement membrane because X-SEQ ID No. 1-Y peptides are capable of increasing the production of integrins and laminins and are compatible for being able to be used as ingredients in a cosmetic composition.

As will be reflected below in the examples, assays have been carried out in which the adhesive effect in skin cells, obtained thanks to the presence of peptides of general formula X-SEQ ID No. 1-Y, as well as an increase in cell proliferation is observed.

Therefore, this increase of cell proliferation together with the adhesive effect obtained with the use of peptides of general formula X-SEQ ID No. 1-Y allow as a result obtaining a more compact epidermis, preventing the loss of firmness which is very characteristic of skin aging.

Another characteristic of aged skin is the loss of contact between cells, giving rise to a lack of nutrition and changes in the skin such as dryness, yellowish complexion and loss of functionality.

These signs of aging can be combated using the cosmetic composition developed according to the present invention including peptides of general formula X-SEQ ID No. 1-Y.

Embodiments

The experiments set forth below are described as a support of particular aspects of the present invention and in no case do they limit the scope thereof.

Example 1

Immunostaining assays have been carried out in human fibroblasts and keratinocytes in order to determine if SEQ ID No. 2 has the ability to enhance the expression of α6 integrin and laminin V (FIGS. 2, 3, 4, and 5).

Given that cells use integrins to recognize laminins, and laminins bind cells with the basement membrane through integrins, a peptide which is able to increase the production of integrins and laminins will enhance cell adhesion and their binding to the basement membrane.

The assay uses a primary (monoclonal) antibody binding to the protein which is intended to be detected (integrin or laminin), and a secondary (polyclonal) antibody binding to the complex between the protein and the primary antibody. The secondary antibody is coupled to a fluorescent compound (FITC-Fluorescein Isothiocyanate).

FITC is illuminated with filtered light at 495 nm (absorption wavelength) and the light emitted by the dye is detected at 528 nm (emission wavelength).

These aspects are observed in FIGS. 2, 3, 4 and 5.

The expression of α6 integrin in human fibroblasts that have not been treated with SEQ ID No. 2 can be observed by immunofluorescence emission in FIG. 2. On the other hand, the increase of the expression of α6 integrin in human fibroblasts treated with SEQ ID No. 2 can also be seen by immunofluorescence emission in FIG. 3.

The difference in the expression of laminin in the presence and absence of SEQ ID No. 2 has been identified in this same assay.

This difference of expression can be observed in FIGS. 4 and 5. The expression of laminin V in human fibroblasts that have not been treated with SEQ ID No. 2 can be observed by immunofluorescence in FIG. 4, and the increase of the expression of laminin V in human fibroblasts treated with SEQ ID No. 2 can also be seen by immunofluorescence emission in FIG. 5.

As a conclusion, a significant increase of laminin V and α6 integrin can be observed in fibroblasts treated with SEQ ID No. 2 but not in keratinocytes. No variation in the production of beta 1 integrin was not detected either.

Example 2

The adhesion process at a cellular level has been determined by means of a in vitro fibroblast culture in the second embodiment assay.

Figure 6:
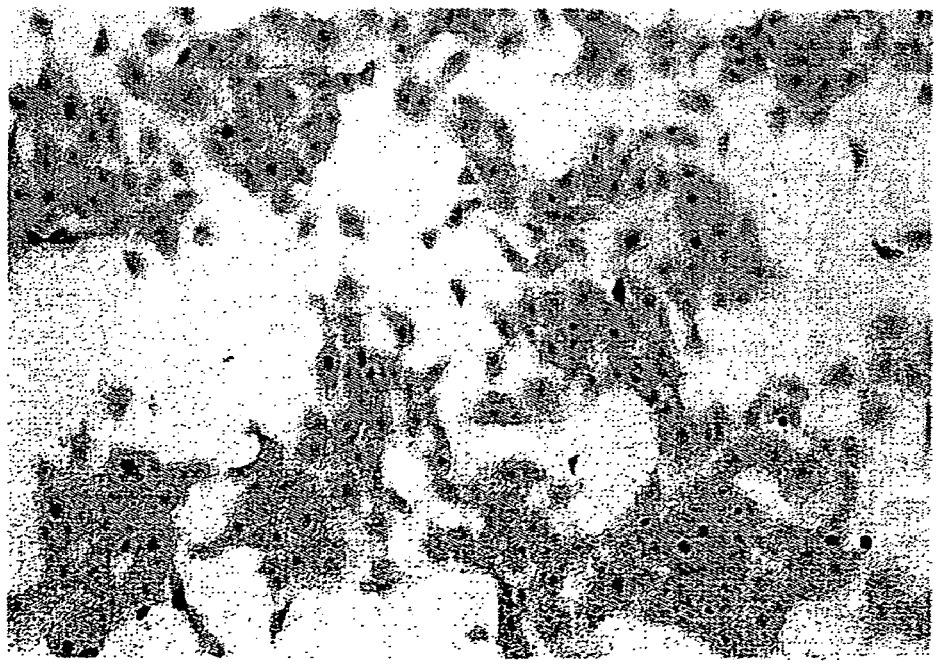
FIG. 6 shows cell adhesion in human fibroblasts for a control sample.
Figure 7:
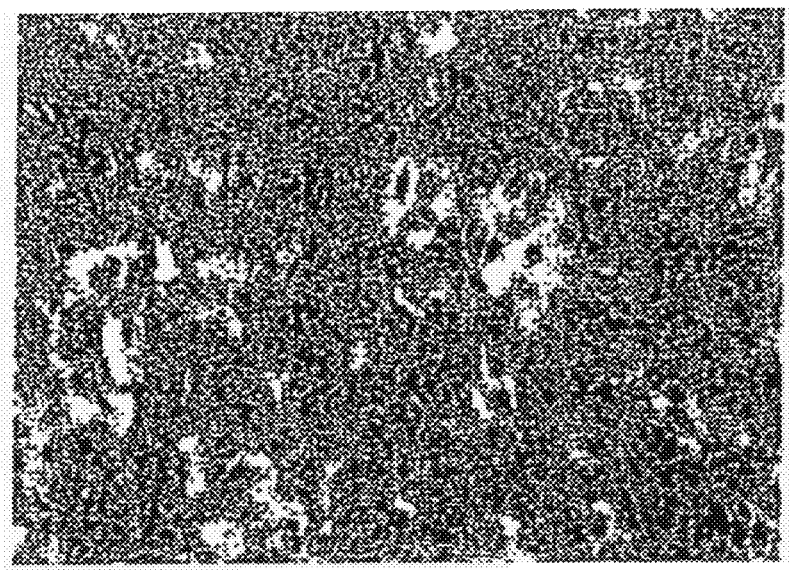
FIG. 7 shows cell adhesion in human fibroblasts treated with SEQ ID NO.2.

This fact is shown in FIGS. 6 and 7.

FIG. 6 shows cell adhesion in human fibroblasts that have not been treated and FIG. 7 shows cell adhesion in fibroblasts treated with SEQ ID No. 2.

FIGS. 6 and 7 show a uniform coating of the assay microwell and the growth and distribution of the fibroblasts that are more related with cell adhesion than with cell proliferation.

In addition to promoting cell adhesion and migration, the cosmetic preparation with SEQ ID No. 2 favors the formation of blood vessels, improving microcirculation.

Example 3

This embodiment shows the in vitro evaluation of the cell adhesion of keratinocytes to peptides of general formula X-SEQ ID no. 1-Y and the comparative evaluation between them.

This embodiment shows how cutaneous cell adhesion increases in the presence of X-SEQ ID No. 1-Y peptides and the comparison of the different variants thereof: SEQ ID No. 2, SEQ ID No. 1, Pal-SEQ ID No 1, and SEQ ID No 2-amino (see FIGS. 8, 9 and 10).

The cell cultures used in the following example are human epidermal keratinocytes (HEKa) in the presence of specific growth factors of keratinocytes.

First, 96 microwells are placed in a plate, they are coated with 50 µL of a peptide of general formula X-SEQ ID NO.1-Y (0.5-250 µg/ml per microwell) in distilled water and dried overnight at room temperature.

On the other hand, control assays are carried out with microwells coated with 40 µM of BSA (bovine serum albumin) so as to evaluate non-specific cell adhesion.

All the microwells have been washed with 200 µL of PBS (phosphate buffered saline) and blocked for 1 hour with 1% BSA in PBS at 37° C.

Trypsin was added to human cutaneous keratinocytes, and they were marked for 30 minutes at 37° C. in calcein-AM at a concentration of 5 µM and they were finally washed three times in Epilife® medium.

The marked cells ($4.5 \times 10^4$/microwell) were added to the plate previously coated with the X-SEQ ID No. 1-Y peptide and were incubated for 2 hours at 37° C. in an atmosphere humidified with 5% $CO_2$.

The cell adhesion was assessed by the measurement of calcein fluorescence before and after the washing.

The percentage of cell adhesion was determined by dividing the fluorescence of adhered cells by the total fluorescence of cells added to each microwell.

The cell adhesion promoted by the X-SEQ ID No. 1-Y peptides was calculated with respect to the non-specific adhesion of the cells to BSA.

Figure 8:
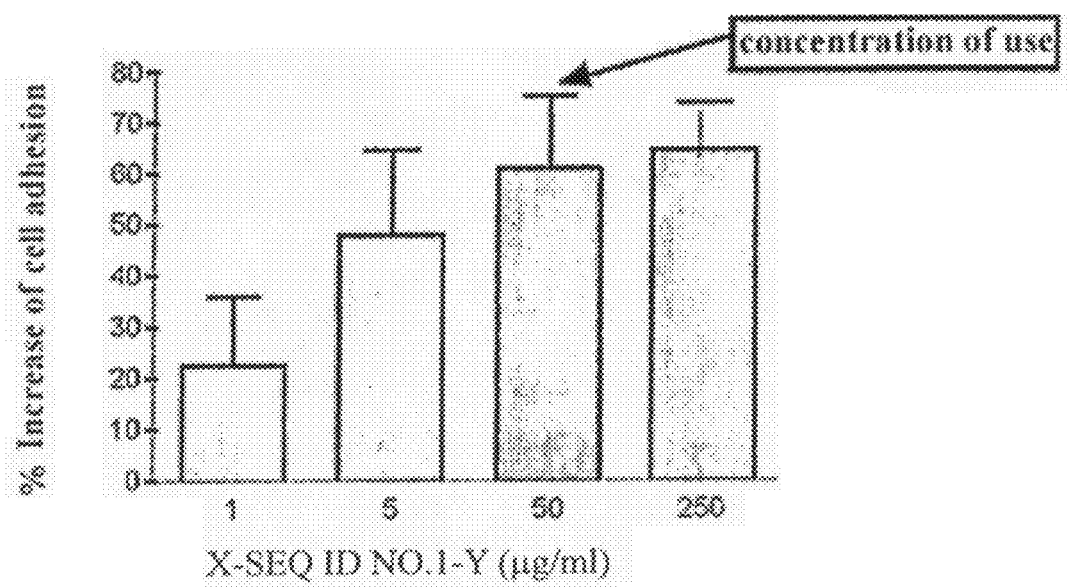
FIG. 8 shows the increase of cell adhesion of keratinocytes at 4 different concentrations for peptide X-SEQ ID NO. 1-Y.
Figure 9:
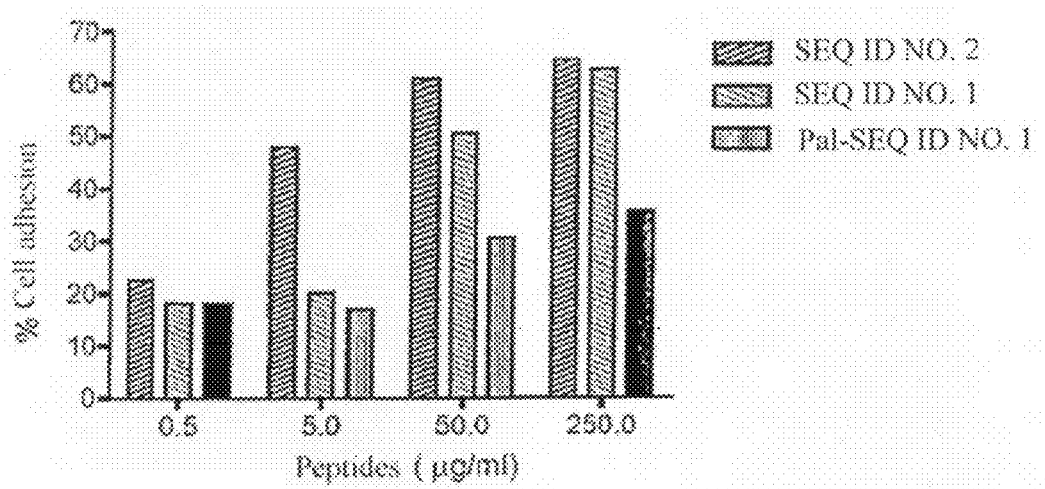
FIG. 9 shows the increase of cell adhesion of keratinocytes at 4 different concentrations for peptides SEQ ID NO.2, SEQ ID NO. 1 and Pal-SEQ ID NO.1.
Figure 10:
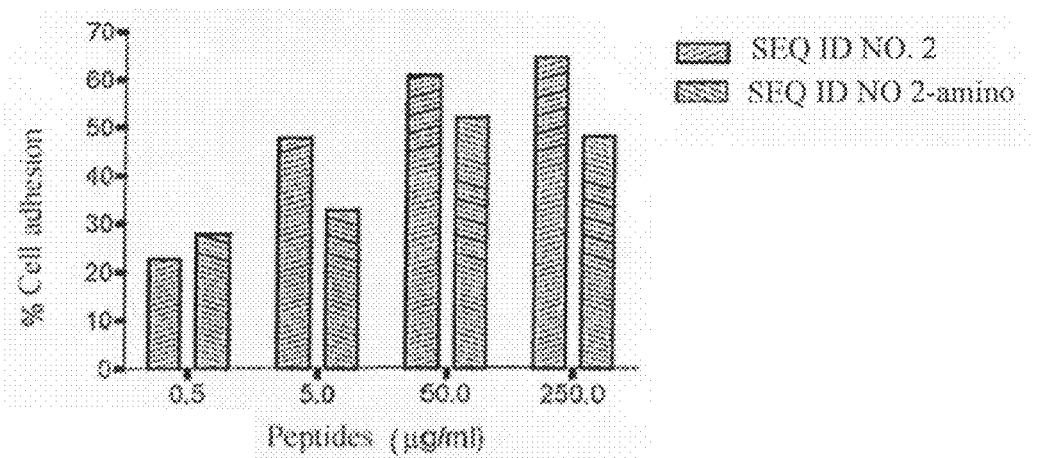
FIG. 10 shows the increase of cell adhesion keratinocytes at 4 different concentrations for peptides SEQ ID NO. 2 and SEQ ID NO. 2-NH$_2$.

The results show that the X-SEQ ID No. 1-Y peptides are capable of promoting keratinocyte adhesion in a dose-dependent manner (see FIGS. 8, 9 and 10).

The cell fixing caused by X-SEQ ID No. 1-Y peptides was 65% with respect to the non-specific adhesion at the highest concentration studied.

These results show that X-SEQ ID No. 1-Y peptides are recognized by specialized receptors in the cell surface.

These findings suggest that the peptides of general formula X-SEQ ID No. 1-Y are good candidates to form part of cosmetic formulations for restructuring and increasing the firmness of the skin.

If FIGS. 8, 9 and 10 are observed and compared, an increase of cell adhesion is observed as the peptide doses increase (dose-dependent).

If the extrapolated results of FIG. 9 are compared, a great increase of keratinocyte cell adhesion is observed in all cases, but there is a peptide producing greater adhesion which is the SEQ ID No. 2 peptide, i.e. the peptide in which X is equal to serine.

FIG. 10 shows the cell adhesion levels of the SEQ ID No. 2 and SEQ ID No. 2-amino peptides where it is observed how the adhesion caused by SEQ ID No. 2-amino is greater at small doses (0.5 µg/ml), and a greater adhesion of the SEQ ID No. 2 peptides is generated at larger doses.

The invention claimed is:

1. A method of increasing firmness of skin and delaying aging of skin, comprising administering to the skin a cosmetic composition, said cosmetic composition including XIKVAV peptides of general formula I X-SEQ ID NO. 1-Y:

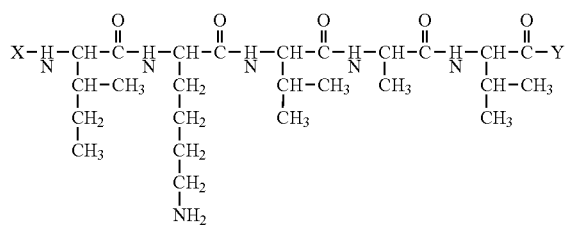

wherein X is selected from the group consisting of hydrogen, an amino acid and an acyl group and Y is selected from the group consisting of amino, hydroxyl and thiol, wherein the XIKVAV peptides of general formula I X-SEQ ID NO. 1-Y stimulate bioadhesion of cutaneous cells by increasing expression of bioadhesion peptides.

2. The method according to claim 1, wherein X is hydrogen or serine.

3. The method according to claim 1, wherein X is palmitoyl or decanoyl.

4. The method according to claim 1, wherein Y is amino.

5. The method according to claim 1, wherein Y is hydroxyl.

6. The method according to claim 1, wherein Y is thiol.

7. The method according to claim 1, wherein the cutaneous cells are keratinocytes.

8. The method according to claim 1, wherein the bioadhesion peptides are alpha 6 integrin and laminin V.

9. The method according to claim 1, wherein the cosmetic composition is selected from the group consisting of a gel, an emulsion, a cream, a lotion, a shampoo, and a serum.

10. The method according to claim 1, wherein the cosmetic composition increases the firmness of skin by increasing adhesion of cutaneous cells in relation to one another and basal lamina.

11. The method according to claim 1, wherein the XIKVAV peptides of general formula I X-SEQ ID NO. 1-Y are present in an amount of up to 12% by weight in the cosmetic composition.

12. The method according to claim 1, wherein the cosmetic composition comprises the following ingredients in the following percentages by weight:

| Peptide | 0.001-10 |
|---|---|
| Petrolatum | 0-10 |
| Triethanolamine | 0-10 |
| BHT | 0-10 |
| Phenoxyethanol | 0-10 |
| Methylparaben | 0-10 |
| Butylparaben | 0-10 |
| Ethylparaben | 0-10 |
| Propylparaben | 0-10 |
| Isobutylparaben | 0-10 |
| Stearic acid | 0-10 |
| Beeswax | 0-10 |
| Carbomer | 0-10 |
| Dimethiconol | 0-10 |
| Cyclomethicone | 0-1 |
| Glycerin | 0-10 |
| Cetylstearic acid | 0-10 |
| Perfume | 0-10 |
| Water | Up to 99.999. |

13. The method according to claim 1, wherein the XIKVAV peptides of general formula I X-SEQ ID NO. 1-Y are present in an amount of up to 5% by weight in the cosmetic composition.

14. The method according to claim 1, wherein the cosmetic composition includes an excipient selected from the group consisting of water, an alcohol, a lecithin, a natural polymer, an artificial polymer, a surfactant, and a preservative.

* * * * *

SEQUENCE LISTING

```
<160> NUMBER OF SEQ ID NOS: 2

<210> SEQ ID NO 1
<211> LENGTH: 5
<212> TYPE: PRT
<213> ORGANISM: Homo sapiens

<400> SEQUENCE: 1

Ile Lys Val Ala Val
1               5

<210> SEQ ID NO 2
<211> LENGTH: 6
<212> TYPE: PRT
<213> ORGANISM: Homo sapiens

<400> SEQUENCE: 2

Ser Ile Lys Val Ala Val
1               5
```